US008765154B2

(12) United States Patent
Bigorra Llosas et al.

(10) Patent No.: US 8,765,154 B2
(45) Date of Patent: Jul. 1, 2014

(54) TRANSPARENT SOFTENING AGENTS

(75) Inventors: Joaquim Bigorra Llosas, Sabadell (ES); Nuria Bonastre Gilabert, Barbera del Valles (ES); Rafael Pi Subirana, Granollers (ES); Gabriela Caldero, Barcelona (ES)

(73) Assignee: Cognis IP Management GmbH, Dusseldorf (DE)

( * ) Notice: Subject to any disclaimer, the term of this patent is extended or adjusted under 35 U.S.C. 154(b) by 1145 days.

(21) Appl. No.: 10/168,286

(22) PCT Filed: Dec. 15, 2000

(86) PCT No.: PCT/EP00/12811
§ 371 (c)(1),
(2), (4) Date: Oct. 22, 2002

(87) PCT Pub. No.: WO01/47489
PCT Pub. Date: Jul. 5, 2001

(65) Prior Publication Data
US 2003/0130162 A1   Jul. 10, 2003

(30) Foreign Application Priority Data
Dec. 24, 1999  (DE) ................................ 199 62 874

(51) Int. Cl.
*A61K 8/06*   (2006.01)
*A61Q 5/02*   (2006.01)

(52) U.S. Cl.
USPC ....... 424/401; 424/70.1; 424/70.28; 510/119; 510/130

(58) Field of Classification Search
USPC ................................ 424/401, 70.24; 554/109
See application file for complete search history.

(56) References Cited

U.S. PATENT DOCUMENTS

| | | | |
|---|---|---|---|
| 4,089,879 A | | 5/1978 | Naskar et al. |
| 4,136,054 A | * | 1/1979 | Petzold et al. ............ 252/301.21 |
| 4,172,887 A | | 10/1979 | Vanlerberghe et al. |
| 5,133,885 A | * | 7/1992 | Contor et al. .................. 510/521 |
| 5,349,106 A | | 9/1994 | Behler et al. |
| 5,670,677 A | | 9/1997 | Ponsati Obiols et al. |
| 5,705,169 A | | 1/1998 | Stein et al. |
| 5,869,716 A | | 2/1999 | Pi Subirana et al. |
| 5,880,299 A | | 3/1999 | Ponsati Obiols et al. |
| 5,886,201 A | * | 3/1999 | Bonastre et al. .............. 554/110 |
| 6,193,960 B1 | | 2/2001 | Metzger et al. |
| 6,432,895 B1 | | 8/2002 | Bigorra et al. |

FOREIGN PATENT DOCUMENTS

| | | |
|---|---|---|
| DE | 1 165 574 | 8/1960 |
| DE | 20 24 051 C3 | 12/1971 |
| DE | 25 00 241 | 7/1976 |
| DE | 30 32 216 A1 | 4/1982 |
| DE | 40 26 184 A1 | 2/1992 |
| DE | 43 08 792 C1 | 3/1993 |
| DE | 44 09 322 C1 | 3/1994 |
| DE | 197 15 835 C1 | 4/1997 |
| DE | 197 51 151 A1 | 5/1999 |
| EP | 0 694 521 B1 | 1/1996 |
| EP | 0 786 250 A1 | 7/1997 |
| EP | 0 818 450 A1 | 1/1998 |
| FR | 2 252 840 | 11/1974 |
| GB | 962919 | 8/1960 |
| GB | 1 333 475 | 5/1970 |
| WO | WO 91/01295 | 2/1991 |
| WO | WO 93/16157 A1 * | 8/1993 |
| WO | WO 99/18178 | 4/1999 |

OTHER PUBLICATIONS

O. Ponsati, C.R. CED-Congress, Barcelona, (1992), pp. 167-179.
R. Puchta et al., "A New Generation of Softeners", Tenside Surf. Det. 30 (1993), pp. 186-191.
M. Brock, "Neue Entwicklungen auf dem Gebiet der Wäscheweichspüler", Tenside Surf. Det. 30 (1993), pp. 394, 396, 398.
R. Lagerman et al., "Synthesis and Performance of Ester Quaternary Biodegradable Softeners", JAOCS, vol. 71, No. 1 (Jan. 1994).
Uwe Ploog, "Kosmetika Aerosole Riechstoffe," Seifen-Öle-Fette-Wachse, 108, (1982) pp. 373-376.
O'Lenick et al. "Amphoteric Surfactants" Happi, Nov. 1986 pp. 70-74, 125-126.
S. Holzman et al. "Amphoteric Surfactants of the Amphoglycinate and Amphocarboxyglycinate Type", Tenside Detergents 23 (1986) 6 pp. 309-313.
Bilbo et al. "Amphoteric Surfactants a Structure Function Study" Soap/Cosmetics/Chemical Specialties for Apr. 1990 pp. 46-50, 114-116.
Busch et al., "Natürliche Bestandteile in Kosmetischen Mittetn", Jan. 1993 Euro Cosmetics, pp. 15-23.
C. Todd et al., "Volatile silicone fluids for cosmetic formulations", Cosmetics and Toiletries, vol. 91, (Jan. 1976), pp. 29-32.
Tronnier et al., "Experimentelle Untersuchungen zur Wirkungsweise aluminiumhaltiger Antiperspiranzien", J. Soc. Cosmetic Chemists 24, 281-290 (1973).
Graham et al. "Inhibition of the mitochondrial oxidation of octanoate by salicylic acid and related compounds", J. Pharm. Pharmac., 1974, 26, pp. 531-534.
R. Lochhead et al., "Encyclopedia of Polymers and Thickeners for Cosmetics", Cosmetics & Toiletries, vol. 108, (May 1993), pp. 95-114, 116-124, 127-130, 132-135.
"Kosmetische Färbemittel", Farbstoffkommission der Deutschen Forschungsgemeinschaft, Verlag Chemie, Weinheim, (1984), pp. 81-106.
DE19751151 Patent Translate from Espacenet.com, 16 pgs, May 1999.
WO9316157 Patent Translate from Espacenet.com, 9 pgs, Aug. 1993.

* cited by examiner

*Primary Examiner* — Lakshmi Channavajjala
(74) *Attorney, Agent, or Firm* — Servilla Whitney LLC

(57) ABSTRACT

The invention relates to transparent softening agents containing: (a) ester quaternaries, which are obtained by reacting alkanolamines with a mixture consisting of fatty acids and of dicarboxylic acids, whereby the resulting esters are optionally alkoxylated and subsequently quaternized in a known manner, and containing; (b) auxiliary agents selected from the group formed by: (b1) fatty acid amidoamines and/or quaternization products thereof; (b2) betaines; (b3) nonionic surfactants; (b4) polyols and/or derivatives thereof; (b5) alcohols and/or; (b6) hydrotropes.

19 Claims, No Drawings

TRANSPARENT SOFTENING AGENTS

FIELD OF THE INVENTION

The invention relates to transparent softening agents comprising special ester quats and auxiliaries, such as fatty acid amidoamines and quaternization products thereof, betaines, nonionic surfactants, polyols and/or derivatives thereof, alcohols and/or hydrotropic agents.

PRIOR ART

The term "ester quats" is generally understood as meaning quaternized fatty acid triethanolamine ester salts, which are widely suitable for softening both fibers and also hair. In former years, these substances have pushed conventional quaternary ammonium compounds, such as, for example, the known distearyldimethyl-ammonium chloride, to a large extent out of the market as the result of a better ecotoxicological compatibility. Overviews on this theme are given, for example, by O. Ponsati in C. R. CED-Congress, Barcelona, 1992, p. 167, R. Puchta et al. in Tens. Surf. Det., 30, 186 (1993), M. Brock in Tens. Surf. Det. 30, 394 (1993) and R. Lagerman et al. in J. Am. Oil. Chem. Soc., 71, 97 (1994).

Although ester quats of the prior art have very good performance properties and satisfactory biodegradability and good skin cosmetic compatibility, the preparations containing ester quats known from the prior art are cloudy.

Consequently, the object of the invention was to provide preparations containing ester quats which, even after storage, did not turn cloudy and at the same time have good softening and antistatic behavior. Furthermore, such preparations should facilitate the ironing of textiles.

DESCRIPTION OF THE INVENTION

The invention provides transparent softening agents comprising
(a) ester quats obtainable by reacting alkanolamines with a mixture of fatty acids and dicarboxylic acids, optionally alkoxylating the resulting esters and then quaternizing them in a manner known per se and
(b) auxiliaries chosen from the group formed by (b1) fatty acid amidoamines and/or quaternization products thereof, (b2) betaines, (b3) nonionic surfactants, (b4) polyols and/or derivatives thereof (b5) alcohols and/or (b6) hydrotropic agents.

Surprisingly, it has been found that by mixing special ester quats with betaines, fatty acid amidoamines (or quaternization products thereof), nonionic surfactants, polyols and/or derivatives thereof, alcohols and/or hydrotropic agents, transparent preparations are obtained which, even after storage, do not turn cloudy and in addition exhibit excellent hair and fiber softening properties. Furthermore, fibers which have been treated with these preparations are significantly easier to iron.

Ester Quats (1) Alkanolamines

Alkanolamines which are suitable for the purposes of the invention as central nitrogen compounds may contain an alkane radical having 1 to 4 carbon atoms. Preference is given to using triethanolamine and products of the addition thereof and 1 to 10 and preferably 2 to 5 mol of ethylene oxide. Also suitable are mixtures of triethanolamines, such as, for example, methyldiethanolamine with triethanolamine and the like.

(2) Fatty Acids

Fatty acids are to be understood as meaning aliphatic carboxylic acids of the formula (I)

$$R^1CO\text{—}OH \quad (I)$$

in which $R^1CO$ is an aliphatic, linear or branched acyl radical having 6 to 22 carbon atoms and 0 and/or 1, 2 or 3 double bonds. Typical examples are caproic acid, caprylic acid, 2-ethylhexanoic acid, capric acid, lauric acid, isotridecanoic acid, myristic acid, palmitic acid, palmoleic acid, stearic acid, isostearic acid, oleic acid, elaidic acid, petroselic acid, linoleic acid, linolenic acid, elaostearic acid, arachidic acid, gadoleic acid, behenic acid and erucic acid, and technical-grade mixtures thereof which are produced, for example, during the pressurized cleavage of natural fats and oils, during the reduction of aldehydes from the Roelen oxo synthesis or the dimerization of unsaturated fatty acids. Preference is given to technical-grade fatty acids having 12 to 18 carbon atoms, such as, for example, coconut, palm, palm kernel or tallow fatty acid, preferably in hydrogenated or partially hydrogenated form.

(3) Dicarboxylic Acids

Dicarboxylic acids which are suitable as feed materials for the purposes of the invention conform to the formula (II),

$$HOOC\text{—}[X]\text{—}COOH \quad (II)$$

in which X is an optionally hydroxy-substituted alkylene group having 1 to 10 carbon atoms. Typical examples are succinic acid, maleic acid, glutaric acid, 1,12-dodecanedioic acid and, in particular, adipic acid.

(4) Esterification

The fatty acids and the dicarboxylic acids can be used in the molar ratio from 1:10 to 10:1. However, it has proven advantageous to set a molar ratio of from 1:1 to 4:1 and in particular 1.5:1 to 3:1. The trialkanolamines on the one hand and the acids, i.e. fatty acids and dicarboxylic acids taken together, can be used in the molar ratio 1:1.2 to 1:2.4. A trialkanolamine:acids molar ratio of from 1:1.5 to 1:1.8 has proven optimal.

The esterification can be carried out in a manner known per se, as is described, for example, in international patent application WO 91/01295. The esterification is advantageously carried out at temperatures of from 120 to 220° C. and in particular 130 to 170° C. and pressures of from 0.01 to 1 bar. Suitable catalysts which have proven successful are hypophosphorous acids and alkali metal salts thereof, preferably sodium hypophosphite, which can be used in amounts of from 0.01 to 0.1% by weight and preferably 0.05 to 0.07% by weight, based on the feed substances. With regard to a particularly high color quality and stability, the co-use of alkali metal and/or alkaline earth metal borohydrides, such as, for example, potassium, magnesium and, in particular, sodium borohydride, has proven advantageous. The cocatalysts are usually used in amounts of from 50 to 1000 and, in particular, 100 to 500 ppm, again based on the feed materials. Corresponding processes are also the subject-matter of the two German patent specifications DE 4308792 C1 and DE 4409322 C1, to the teaching of which reference is expressly made here. It is possible to use mixtures of the fatty acids and dicarboxylic acids, or else to carry out the esterification with the two components one after the other.

(5) Alkoxylation

To prepare polyalkylene oxide-containing ester quats, it is possible to use two alternatives. Firstly, ethoxylated trialkanolamines can be used. This has the advantage that the alkyleneoxy distribution in the subsequently resulting ester quat with regard to the three OH groups of the amine is approximately equal. However, a disadvantage is that the esterification becomes more difficult for steric reasons. The method of choice therefore consists in alkoxylating the ester prior to quaternization. This can be carried out in a manner known per se, i.e. in the presence of basic catalysts and at elevated temperatures. Suitable catalysts are, for example, alkali metal and alkaline earth metal hydroxides and alkoxides, preferably sodium hydroxide and, in particular sodium methoxide; the feed amount is usually 0.5 to 5% by weight and preferably 1 to 3% by weight, based on the feed materials. If these catalysts are used, free hydroxyl groups are primarily alkoxylated. If, however, the catalysts used are calcined hydrotalcites or hydrotalcites hydrophobicized with fatty acids, insertion of the alkylene oxides into the ester bonds also occurs. This method is preferred if an alkylene oxide distribution is desired which is close to that when alkoxylated trialkanolamines are used. The alkylene oxides used may be ethylene oxide and propylene oxide, and mixtures thereof (random or block distribution). The reaction is usually carried out at temperatures in the range from 100 to 180° C. The incorporation of, on average, 1 to 10 mol of alkylene oxide per mole of ester increases the hydrophilicity of the ester quats, improves the solubility and decreases the reactivity toward anionic surfactants.

(6) Quaternization and Alkylating Agents

The quaternization of the fatty acid/dicarboxylic acid trialkanolamine ester can be carried out in a manner known per se. Although the reaction with the alkylating agents can also be carried out in the absence of solvents, the co-use of at least small amounts of water or lower alcohols, preferably isopropyl alcohol, is recommended for the preparation of concentrates which have a solids content of at least 80% by weight and in particular at least 90% by weight.

Suitable alkylating agents are alkyl halides, such as, for example, methyl chloride, dialkyl sulfates, such as, for example, dimethyl sulfate or diethyl sulfate, or dialkyl carbonates, such as, for example, dimethyl carbonate or diethyl carbonate.

The esters and the alkylating agents are usually used in the molar ratio 1:0.95 to 1:1.05, i.e. in virtually stoichiometric amounts. The reaction temperature is usually 40 to 80° C. and in particular 50 to 60° C. After the reaction, it is advisable to destroy unreacted alkylating agent by adding, for example, ammonia, an (alkanol)amine, an amino acid or an oligopeptide, as is described, for example, in German patent application DE 4026184 A1.

The agents according to the invention can comprise the ester quats in amounts of from 5 to 70% by weight, preferably 15 to 60% by weight and in particular 30 to 40% by weight, based on the final concentration.

Auxiliaries

Auxiliaries which are suitable for the purposes of the invention as component (b) prevent preparations comprising ester quats becoming cloudy upon storage and thus unstable. Suitable stabilizers are fatty acid amidoamines and/or quaternization products thereof, betaines, nonionic surfactants and/or polyols.

Fatty Acid Amidoamines and/or Quaternization Products Thereof

Fatty acid amidoamines which are suitable as component (b1) represent condensation products of fatty acids with optionally ethoxylated di- or oligoamines, which preferably conform to the formula (III),

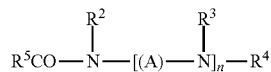

(III)

in which $R^5CO$ is a linear or branched, saturated or unsaturated acyl radical having 6 to 22 carbon atoms, $R^2$ is hydrogen or an optionally hydroxy-substituted alkyl radical having 1 to 4 carbon atoms, $R^3$ and $R^4$, independently of one another, are hydrogen, a $(CH_2CH_2O)_mH$ group or an optionally hydroxy-substituted alkyl radical having 1 to 4 carbon atoms, A is a linear or branched alkylene group having 1 to 6 carbon atoms, n is a number from 1 to 4 and m is a number from 1 to 30. Typical examples are condensation products of caproic acid, caprylic acid, 2-ethylhexanoic acid, capric acid, lauric acid, isotridecanoic acid, myristic acid, palmitic acid, palmoleic acid, stearic acid, isostearic acid, oleic acid, elaidic acid, petroselic acid, linoleic acid, linolenic acid, elaostearic acid, arachidic acid, gadoleic acid, behenic acid and erucic acid, and technical-grade mixtures thereof with ethylenediamine, propylenediamine, diethylenetriamine, dipropylenetriamine, triethylenetetramine, tripropylenetetramine, and adducts thereof with 1 to 30, preferably 5 to 15 and in particular 8 to 12, mol of ethylene oxide. The use of ethoxylated fatty acid amidoamines here is preferred because the hydrophilicity of the emulsifiers can in this way be adjusted exactly to the active ingredients to be emulsified. In place of the fatty acid amidoamines, it is also possible to use the quaternization products thereof, which are obtained by reacting the amidoamines with suitable alkylating agents, such as, for example, methyl chloride or, in particular, dimethyl sulfate, in accordance with processes known per se. The quaternization products preferably conform to the formula (IV),

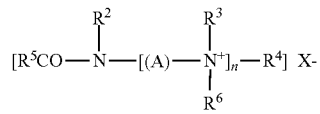

(IV)

in which $R^5CO$ is a linear or branched, saturated or unsaturated acyl radical having 6 to 22 carbon atoms, $R^2$ is hydrogen or an optionally hydroxy-substituted alkyl radical having 1 to 4 carbon atoms, $R^3$ is hydrogen, a $(CH_2CH_2O)_mH$ group or an optionally hydroxy-substituted alkyl radical having 1 to 4 carbon atoms, $R^4$ is $R^5CO$, hydrogen, a $(CH_2CH_2O)_mH$ group or an optionally hydroxy-substituted alkyl radical having 1 to 4 carbon atoms, $R^6$ is an alkyl radical having 1 to 4 carbon atoms, A is a linear or branched alkylene group having 1 to 6 carbon atoms, n is a number from 1 to 4, m is a number from 1 to 30 and X is halide, specifically chloride, or alkylsulfate, preferably methylsulfate. Suitable for this purpose are, for example, the methylation products of the preferred fatty acid amidoamines already given above. In addition, it is also possible to use mixtures of fatty acid amidoamines and quaternization products thereof, which are prepared in a particularly simple manner by not carrying out the quaternization completely, but only to a desired degree.

The agents according to the invention can comprise the fatty acid amidoamines and/or quaternization products thereof in amounts of from 0.1 to 50% by weight, preferably 1 to 30% by weight and in particular 2 to 10% by weight, based on the final concentration.

Betaines

Betaines which are suitable as component (b2) represent known surfactants which are primarily prepared by carboxyalkylation, preferably carboxylmethylation, of aminic compounds. The starting materials are preferably condensed with halocarboxylic acids or salts thereof, in particular with sodium chloroacetate, one mole of salt being formed per mole of betaine. Also, the addition of unsaturated carboxylic acids, such as, for example, acrylic acid, is also possible. With regard to nomenclature and, in particular, to differentiate between betaines and "true" amphoteric surfactants, reference is made to the contribution by U. Ploog in Seifen-Öle-Fette-Wachse, 108, 373 (1982). Further overviews on this theme are given, for example, by A. O'Lennick et al. in HAPPI, November 70 (1986), S. Holzman et al. in Tens. Surf. Det. 23, 309 (1986), R. Bibo et al. in Soap Cosm. Chem. Spec., April 46 (1990) and P. Ellis et al. in Euro Cosm. 1, 14 (1994). Examples of suitable betaines are the carboxyalkylation products or secondary and in particular tertiary amines which conform to the formula (IV),

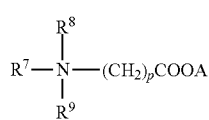

in which $R^7$ is alkyl and/or alkenyl radicals having 6 to 22 carbon atoms, $R^8$ is hydrogen or alkyl radicals having 1 to 4 carbon atoms, $R^9$ is alkyl radicals having 1 to 4 carbon atoms, p is a number from 1 to 6 and A is an alkali metal and/or alkaline earth metal or ammonium. Typical examples are the carboxymethylation products of hexylmethylamine, hexyldimethylamine, octyldimethylamine, decyldimethylamine, dodecylmethylamine, dodecyldimethylamine, dodecylethylmethylamine, $C_{12/14}$-cocoalkyldimethylamine, myristyldimethylamine, cetyldimethylamine, stearyldimethylamine, stearylethylmethylamine, oleyldimethylamine, $C_{16/18}$-tallow-alkyl-dimethylamine, and technical-grade mixtures thereof. Also suitable are carboxyalkylation products of amidoamines, which conform to the formula (VI),

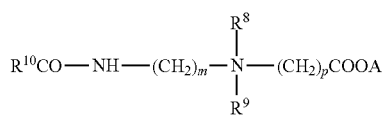

in which $R^{10}CO$ is an aliphatic acyl radical having 6 to 22 carbon atoms and 0 or 1 to 3 double bonds, m is a number from 1 to 3 and $R^8$, $R^9$, p and A have the meanings given above. Typical examples are reaction products of fatty acids having 6 to 22 carbon atoms, namely caproic acid, caprylic acid, capric acid, lauric acid, myristic acid, palmitic acid, palmoleic acid, stearic acid, isostearic acid, oleic acid, elaidic acid, petroselic acid, linoleic acid, linolenic acid, elaostearic acid, arachidic acid, gadoleic acid, behenic acid and erucic acid, and technical-grade mixtures thereof with N,N-dimethylaminoethylamine, N,N-dimethylaminopropyl-amine, N,N-diethylaminoethylamine and N,N-diethylaminopropylamine which are condensed with sodium chloroacetate. Preference is given to the use of a condensation product of $C_{8/18}$-coconut fatty acid-N,N-dimethylaminopropylamide with sodium chloroacetate.

Further suitable starting materials for the betaines to be used for the purposes of the invention are imidazolines, which conform to the formula (VII),

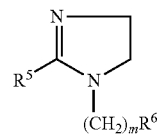

in which $R^5$ is an alkyl radical having 5 to 21 carbon atoms, $R^6$ is a hydroxy group, an $OCOR^5$ or $NHCOR^5$ radical and m is 2 or 3. These substances too are known substances which can be obtained, for example, by cyclizing condensation of 1 or 2 mol of fatty acid with polyfunctional amines, such as, for example, aminoethylethanolamine (AEEA) or diethylenetriamine. The corresponding carboxyalkylation products are mixtures of different open-chain betaines. Typical examples are condensation products of the abovementioned fatty acids with AEEA, preferably imidazolines based on lauric acid or again $C_{12/14}$-coconut fatty acid, which are then betainized with sodium chloroacetate.

The agents according to the invention can comprise the betaines in amounts of from 0.1 to 50% by weight, preferably 1 to 30% by weight and in particular 2 to 10% by weight, based on the final concentration.

Nonionic Surfactants

Suitable nonionogenic surfactants which form component (b3) come from at least one of the following groups:

addition products of from 2 to 50 mol of ethylene oxide and/or 0 to 5 mol of propylene oxide onto linear fatty alcohols having 8 to 22 carbon atoms, onto fatty acids having 8 to 22 carbon atoms, onto alkylphenols having 8 to 15 carbon atoms in the alkyl group, and alkylamines having 8 to 22 carbon atoms in the alkyl radical;

alkyl and/or alkenyl oligoglycosides having 8 to 22 carbon atoms in the alk(en)yl radical and ethoxylated analogues thereof;

addition products of from 1 to 15 mol of ethylene oxide onto castor oil and/or hydrogenated castor oil;

addition products of from 15 to 60 mol of ethylene oxide onto castor oil and/or hydrogenated castor oil;

partial esters of glycerol and/or sorbitan with unsaturated, linear or saturated, branched fatty acids having 12 to 22 carbon atoms and/or hydroxycarboxylic acids having 3 to 18 carbon atoms, and adducts thereof with 1 to 30 mol of ethylene oxide;

partial esters of polyglycerol (average intrinsic degree of condensation 2 to 8), polyethylene glycol (molecular weight 200 to 5000), trimethylolpropane, pentaerythritol, sugar alcohols (e.g. sorbitol), alkyl glucosides (e.g. methyl glucoside, butyl glucoside, lauryl glucoside), and polyglucosides (e.g. cellulose) with saturated and/or unsaturated, linear or branched fatty acids having 12 to 22 carbon atoms and/or hydroxycarboxylic acids having 3 to 18 carbon atoms, and adducts thereof with 1 to 30 mol of ethylene oxide;

mixed esters of pentaerythritol, fatty acids, citric acid and fatty alcohol as in German patent DE 1165574 and/or mixed esters of fatty acids having 6 to 22 carbon atoms, methylglucose and polyols, preferably glycerol or polyglycerol;

mono-, di- and trialkyl phosphates, such as mono-, di- and/or tri-PEG-alkyl phosphates and salts thereof;

wool wax alcohols;
polysiloxane-polyalkyl-polyether copolymers and corresponding derivatives and
polyalkylene glycols.

The addition products of ethylene oxide and/or of propylene oxide onto fatty alcohols, fatty acids, alkylphenols onto castor oil are known, commercially available products. These are homologue mixtures whose average degree of alkoxylation corresponds to the ratio of the quantitative amounts of ethylene oxide and/or propylene oxide and substrate with which the addition reaction is carried out. $C_{12/18}$-fatty acid mono- and diesters of addition products of ethylene oxide onto glycerol are known from German patent DE 2024051 as refatting agents for cosmetic preparations.

Alkyl and/or alkenyl oligoglycosides, their preparation and their use are known from the prior art. They are prepared, in particular, by reacting glucose or oligosaccharides with primary alcohols having 8 to 18 carbon atoms. With regard to the glycoside radical, both monoglycerides, in which a cyclic sugar radical is glycosidically bonded to the fatty alcohol, and also oligomeric glycosides having a degree of oligomerization of up to, preferably, about 8, are suitable. The degree of oligomerization here is a statistical average value which is based on a homologue distribution customary for such technical-grade products.

Typical examples of suitable partial glycerides are hydroxystearic acid monoglyceride, hydroxystearic acid diglyceride, isostearic acid monoglyceride, isostearic acid diglyceride, oleic acid monoglyceride, oleic acid diglyceride, ricinoleic acid moglyceride, ricinoleic acid diglyceride, linoleic acid monoglyceride, linoleic acid diglyceride, linolenic acid monoglyceride, linolenic acid diglyceride, erucic acid monoglyceride, erucic acid diglyceride, tartaric acid monoglyceride, tartaric acid diglyceride, citric acid monoglyceride, citric diglyceride, malic acid monoglyceride, malic acid diglyceride and technical-grade mixtures thereof which may also comprise small amounts of triglyceride a minor product of the preparation process. Likewise suitable are addition products of from 1 to 30 mol, preferably 5 to 10 mol, of ethylene oxide onto said partial glycerides.

Typical examples of suitable sorbitan esters are sorbitan monoisostearate, sorbitan sesquiisostearate, sorbitan diisostearate, sorbitan trlisostearate, sorbitan monooleate, sorbitan sesquioleate, sorbitan dioleate, sorbitan trioleate, sorbitan monoerucate, sorbitan sesquierucate, sorbitan dierucate, sorbitan trierucate, sorbitan mononcinoleate, sorbitan sesquiricinoleate, sorbitan diricinoleate, sorbitan triricinoleate, sorbitan mono hydroxystearate, sorbitan sesquihydroxystearate, sorbitan dihydroxystearate, sorbitan trihydroxystearate, sorbitan monotartrate, sorbitan sesquitartrate, sorbitan ditartrate, sorbitan tritartrate, sorbitan monocitrate, sorbitan sesquicitrate, sorbitan dicitrate, sorbitan tricitrate, sorbitan monomaleate, sorbitan sesquimaleate, sorbitan dimaleate, sorbitan trimaleate and technical-grade mixtures thereof. Also suitable are addition products of from 1 to 30 mol, preferably 5 to 10 mol, of ethylene oxide onto said sorbitan esters.

Typical examples of suitable polyglycerol esters are Polyglycerol-2 Dipolyhydroxystearate (Dehymuls® PGPH), Polyglycerol-3 Diisostearate (Lameform® TGI), Polyglycerol-4 Isostearate (Isolan® GI 34), Polyglycerol-3 Oleate, Diisostearoyl Polyglycerol-3 Diisostearate (Isolan® PDI), Polyglycerol-3 Methylglucose Distearate (Tego Care® 450), Polyglycerol-3 Beeswax (Cera Bellina®), Polyglycerol-4 Caprate (Polyglycerol Caprate T2010/90), Polyglycerol-3 Cetyl Ether (Chimexane® NL), Polyglycerol-3 Distearate (Cremophor® GS 32) and Polyglyceryl Polyricinoleate (Admul® WOL 1403) Polyglyceryl Dimerate Isostearate and mixtures thereof.

Examples of further suitable polyol esters are the mono-, di- and triesters of trimethylolpropane or pentaerythritol with lauric acid, coconut fatty acid, tallow fatty acid, palmitic acid, stearic acid, oleic acid, behenic acid and the like, optionally reacted with 1 to 30 mol of ethylene oxide.

The agents according to the invention can comprise the nonionic surfactants in amounts of from 0.1 to 50% by weight, preferably 1 to 30 and in particular 2 to 10% by weight, based on the final concentration.

Polyols and/or Derivatives Thereof

Polyols which are suitable as component (b4) preferably have 2 to 15 carbon atoms and at least two hydroxyl groups. The polyols can also contain further functional groups, in particular amino groups, or be modified with nitrogen. Typical examples are glycerol;
alkylene glycols, such as, for example, ethylene glycol, diethylene glycol, propylene glycol, butylene glycol, hexylene glycol, and polyethylene glycols with an average molecular weight of from 100 to 1000 daltons;
technical-grade oligoglycerol mixtures with an intrinsic degree of condensation of from 1.5 to 10, such as, for example, technical-grade diglycerol mixtures with a diglycerol content of from 40 to 50% by weight;
Methylol compounds, such as, in particular, trimethylolethane, trimethylolpropane, trimethylolbutane, pentaerythritol and dipentaerythritol;
lower alkyl glucosides, in particular those with 1 to 8 carbons in the alkyl radical, such as, for example, methyl and butyl glucoside;
sugar alcohols having 5 to 12 carbon atoms, such as, for example, sorbitol or mannitol,
sugars having 5 to 12 carbon atoms, such as, for example, glucose or sucrose;
amino sugars, such as, for example, glucamine;
dialcohol amines, such as diethanolamine or 2-amino-1,3-propanediol and/or derivatives thereof, such as C1 to C4 ethers, e.g. butyldiglycol methyl ether and/or C1 to C4 carbonates, e.g. propylene glycol carbonate, glycerol carbonate etc. Preference is given to using glycerol, propylene glycol, butylene glycol, hexylene glycol and polyethylene glycols with an average molecular weight in the range from 100 to 1000 daltons. The agents according to the invention can comprise the polyols in amounts of from 0.1 to 50% by weight, preferably 1 to 30% by weight and in particular 2 to 10% by weight, based on the final concentration.

Alcohols

Suitable alcohols for the purposes of the invention are methanol, ethanol, propanol, butanol and/or derivatives thereof. The agents according to the invention can comprise the alcohols in amounts of from 0.1 to 50% by weight, preferably 1 to 30% by weight and in particular 2 to 10% by weight, based on the final concentration.

Hydrotropic Agents

Suitable hydrotropic agents for the purposes of the invention are aromatic alkyl sulfonates, such as, preferably, toluenesulfonates, cumenesulfonates, xylenesulfonates etc. The agents according to the invention can comprise the hydrotropic agents in amounts of from 0.1 to 50% by weight, preferably 1 to 30% by weight and in particular 2 to 10% by weight, based on the final concentration.

INDUSTRIAL APPLICABILITY

In a preferred embodiment of the invention, the transparent softening agents comprise, based on the final concentration, (a) 5 to 90% by weight, preferably 15 to 80% by weight and in particular 30 to 40% by weight of ester quats,
(b) 0.1 to 50% by weight, preferably 1 to 30% by weight and in particular 2 to 10% by weight, of auxiliaries
with the proviso that the quantitative amounts are made up to 100% by weight with water and optionally further auxiliaries and additives.

The softening agents according to the invention can be used for the preparation of cosmetic and/or pharmaceutical cleaners for the softening of hair, such as, for example, creams, gels, lotions, emulsions, wax/fat compositions, or ointments, and also for the preparation of cleaners, preferably laundry detergents, fabric softeners and the like. They can also comprise, as further additives, mild surfactants, oil components, emulsifiers, superfatting agents, pearlescent waxes, body agents, thickeners, polymers, silicone compounds, fats, waxes, stabilizers, biogenic active ingredients, deodorant active ingredients, antidandruff agents, film formers, swelling agents, further UV light protection factors, antioxidants, hydrotropic agents, preservatives, insect repellents, self-tanning agents, solubilizers, perfume oils, dyes, antimicrobial agents and the like.

Typical examples of suitable mild, i.e. particularly skin compatible, surfactants are fatty alcohol polyglycol ether sulfates, monoglyceride sulfates, mono- and/or dialkyl sulfosuccinates, fatty acid isethionates, fatty acid sarcosinates, fatty acid taurides, fatty acid glutamates, α-olefinsulfonates, ether carboxylic acids, alkyl oligoglucosides, fatty acid glucamides, alkylamidobetaines and/or protein fatty acid condensates, the latter preferably being based on wheat proteins.

Suitable oil components of the required polarity are, in particular, Guerbet alcohols based on fatty alcohols having 6 to 18, preferably 8 to 10, carbon atoms, esters of branched $C_6$-$C_{13}$-carboxylic acids with linear $C_6$-$C_{22}$-fatty alcohols, esters of linear $C_6$-$C_{22}$-fatty acids with branched alcohols, in particular 2-ethylhexanol, esters of hydroxycarboxylic acids with linear or branched $C_6$-$C_{22}$-fatty alcohols, in particular Dioctyl Malate, esters of linear and/or branched fatty acids with polyhydric alcohols (such as, for example, propylene glycol, dimerdiol or trimertriol) and/or Guerbet alcohols, liquid mono-/di-/triglyceride mixtures based on $C_6$-$C_{18}$-fatty acids, esters of $C_6$-$C_{22}$-fatty alcohols and/or Guerbet alcohols with aromatic carboxylic acids, in particular benzoic acid, esters of $C_2$-$C_{12}$-dicarboxylic acid with linear or branched alcohols having 1 to 22 carbon atoms or polyols having 2 to 10 carbon atoms and 2 to 6 hydroxyl groups, branched primary alcohols, substituted cyclohexanes, linear and branched $C_6$-$C_{22}$-fatty alcohol carbonates, Guerbet carbonates, esters of benzoic acid with linear and/or branched $C_6$-$C_{22}$-alcohols (e.g. Finsolv® TN), linear or branched, symmetrical or asymmetrical dialkyl ethers having 6 to 22 carbon atoms per alkyl group, ring-opening products of epoxidized fatty acid esters with polyols.

Superfatting agents which can be used are substances such as, for example, lanolin and lecithin, and polyethoxylated or acylated lanolin and lecithin derivatives, polyol fatty acid esters, monoglycerides and fatty acid alkanolamides, the latter also serving as foam stabilizers.

Suitable pearlescent waxes are, for example: alkylene glycol esters, particularly ethylene glycol distearates; fatty acid alkanolamides, specifically coconut fatty acid diethanolamide; partial glycerides, specifically stearic acid monoglyceride; esters of polyhydric, optionally hydroxy-substituted carboxylic acids with fatty alcohols having 6 to 22 carbon atoms, specifically long-chain esters of tartaric acid; fatty substances, such as, for example, fatty alcohols, fatty ketones, fatty aldehydes, fatty ethers and fatty carbonates which have at least 24 carbon atoms, in total, specifically laurone and distearyl ether; fatty acids, such as stearic acid, hydroxystearic acid or behenic acid, ring-opening products of olefin epoxides having 12 to 22 carbon atoms with fatty alcohols having 12 to 22 carbon atoms and/or polyols having 2 to 15 carbon atoms and 2 to 10 hydroxyl groups, and mixtures thereof.

Suitable bodying agents are primarily fatty alcohols or hydroxy fatty alcohols having 12 to 22, and preferably 16 to 18 carbon atoms, and also partial glycerides, fatty acids or hydroxy fatty acids. Preference is given to a combination of these substances with alkyl oligoglucosides and/or fatty acid N-methylglucamides of identical chain length and/or polyglycerol poly-12-hydroxystearates. Suitable thickeners are, for example, Aerosil grades (hydrophilic silicas), polysaccharides, in particular xanthan gum, guar guar, agar agar, alginates and Tyloses, carboxylmethylcellulose and hydroxyethylcellulose, and also relatively high molecular weight polyethylene glycol mono- and diesters of fatty acids, polyacrylates, (e.g. Carbopols® from Goodrich or Synthalene® from Sigma), polyacrylamides, polyvinyl alcohol and polyvinylpyrrolidone, surfactants, such as, for example, ethoxylated fatty acid glycerides, esters of fatty acids with polyols, such as, for example, pentaerythritol or trimethylolpropane, fatty alcohol ethoxylates with narrowed homologue distribution or alkyl oligoglucosides, and electrolytes such as sodium chloride and ammonium chloride.

Suitable cationic polymers are, for example, cationic cellulose derivatives, such as, for example, a quaternized hydroxyethylcellulose available under the name Polymer JR 400® from Amerchol, cationic starch, copolymers of diallylammonium salts and acrylamides, quaternized vinylpyrrolidone/vinylimidazole polymers, such as, for example, Luviquat® (BASF), condensation products of polyglycols and amines, quaternized collagen polypeptides, such as, for example, lauryldimonium hydroxylpropyl hydrolyzed collagen (Lamequat®L/Grünau), quaternized wheat polypeptides, polyethyleneimine, cationic silicone polymers, such as, for example, amidomethicones, copolymers of adipic acid and dimethylaminohydroxylpropyldiethylenetriamine (Cartaretine®/Sandoz), copolymers of acrylic acid or dimethyldiallylammonium chloride (Merquat® 550/Chemviron), polyaminopolyamides, as described, for example, in FR 2252840 A, and crosslinked water-soluble polymers thereof, cationic chitin derivatives, such as, for example, quaternized chitosan, optionally in microcrystalline dispersion, condensation products from dihaloalkyls, such as, for example, dibromobutane with bisdialkylamines, such as, for example, bis-dimethylamino-1,3-propane, cationic guar gum, such as, for example, Jaguar® CBS, Jaguar® C17, Jaguar® C-16 from Celanese, quaternized ammonium salt polymers, such as, for example, Mirapol® A-15, Mirapol® AD-1, Mirapol® AZ-1 from Miranol.

Suitable anionic, zwitterionic, amphoteric and nonionic polymers are, for example, vinyl acetate/crotonic acid copolymers, vinylpyrrolidone/vinyl acrylate copolymers, vinyl acetate/butyl maleate/isobornyl acrylate copolymers, methyl vinyl ether/maleic anhydride copolymers and esters thereof, uncrosslinked polyacrylic acids and polyacrylic acids crosslinked with polyols, acrylamido-propyltrimethylammonium chloride/acrylate copolymers, octylacrylamide/methyl methacrylate/tert-butylamino-ethyl methacrylate/2-hydroxylpropylmethacrylate copolymers, polyvinylpyrrolidone, vinylpyrrolidone/vinyl acetate copolymers, vinylpyrrolidone/dimethylaminoethyl methacrylate/vinylcaprolactam terpolymers, and optionally derivatized cellulose ethers and silicones.

Suitable silicone compounds are, for example, dimethylpolysiloxanes, methylphenylpolysiloxanes, cyclic silicones, and amino-, fatty acid-, alcohol-, polyether-, epoxy-, fluoro-, glucoside- and/or alkyl-modified silicone compounds which can either be liquid or in resin form at room temperature. Also suitable are simethicones, which are mixtures of dimethicones having an average chain length of from 200 to 300 dimethylsiloxane units and hydrogenated silicates. A detailed review of suitable volatile silicones can also be found in Todd et al. in Cosm. Toil. 91, 27 (1976).

Typical examples of fats are glycerides, and suitable waxes are, inter alia, beeswax, carnauba wax, candelilla wax, montan wax, paraffin wax, hydrogenated castor oils, fatty acid esters solid at room temperature or microcrystalline waxes optionally in combination with hydrophilic waxes, e.g. cetyl-stearyl alcohol or partial glycerides. Stabilizers which can be used are metal salts of fatty acids, such as, for example, magnesium, aluminum and/or zinc stearate or ricinoleate.

Biogenic active ingredients are to be understood as meaning, for example, tocopherol, tocopherol acetate, tocopherol palmitate, ascorbic acid, deoxyribonucleic acid, retinol, bisabolol, allantoin, phytantriol, panthenol, AHAs, amino acids, ceramides, psuedoceramides, essential oils, plant extracts and vitamin complexes.

Suitable deodorant active ingredients are, for example, antiperspirants, such as, for example, aluminum chlorohydrates. These are colorless, hygroscopic crystals which readily deliquesce in air and produce aluminum chloride solutions upon evaporation. Aluminum chlorohydrate is used for the preparation of antiperspirant and deodorizing preparations and probably acts via the partial closure of the sweat glands by protein and/or polysaccharide precipitation [cf. J. Soc. Cosm. Chem. 24, 281 (1973)]. For example, an aluminum chlorohydrate is available commercially under the name Locron® from Hoechst AG, Frankfurt/FRG, which corresponds to the formula $[Al_2(OH)_5Cl]*2.5H_2O$ and its use is particularly preferred [cf. J. Pharm. Pharmacol. 26, 531 (1975)]. In addition to the chlorohydrate, it is also possible to use aluminum hydroxylactates and acidic aluminum/zirconium salts. Other deodorant active ingredients which may be added are esterase inhibitors. These are preferably trialkyl citrates, such as trimethyl citrate, tripropyl citrate, triisopropyl citrate, tributyl citrate and in particular triethyl citrate (Hydagen® CAT, Henkel KGaA, Düsseldorf/FRG). The substances inhibit enzyme activity, thus reducing the formation of odor. Presumably, in this process, the cleavage of the citric ester results in the release of the free acid, which lowers the pH on the skin sufficiently for the enzymes to be inhibited. Other substances which are suitable as esterase inhibitors are sterol sulfates or phosphates, such as, for example, lanosterol, cholesterol, campesterol, stigmasterol and sitostearol sulfate and phosphate, dicarboxylic acids and esters thereof, such as, for example, glutaric acid, monoethyl glutarate, diethyl glutarate, adipic acid, monoethyl adipate, diethyl adipate, malonic acid and diethyl malonate, hydroxy carboxylic acids and esters thereof, such as, for example, citric acid, maleic acid, tartaric acid or diethyl tartrate. Antibacterial active ingredients which influence the bacterial flora and destroy bacteria which decompose perspiration or inhibit them in their growth, can likewise be present in the stick preparations. Examples thereof are chitosan, phenoxyethanol and chlorhexidine gluconate. 5-Chloro-2-(2,4-dichlorophenoxy)phenol, which is sold under the trade name Irgasan® by Ciba-Geigy, Basle/CH, has proven particularly effective.

Antidandruff agents which can be used are climbazole, octopirox and zinc pyrethione. Customary film formers are, for example, chitosan, microcrystalline chitosan, quaternized chitosan, polyvinylpyrrolidone, vinylpyrrolidone-vinyl acetate copolymers, polymers of the acrylic acid series, quaternary cellulose derivatives, collagen, hyaluronic acid and salts thereof and similar compounds.

Possible swelling agents for aqueous phases are montmorillonites, clay mineral substances, pemulen, and alkyl-modified Carbopol grades (Goodrich). Further suitable polymers and swelling agents are given in the overview by R. Lochhead in Cosm. Toil. 108, 95 (1993).

UV light protection factors are to be understood as meaning, for example, organic substances (light protection filters) which are in liquid or crystalline form at room temperature and which are able to absorb ultraviolet radiation and give off the absorbed energy again in the form of longer-wave radiation, e.g. heat. UVB filters can be oil-soluble or water-soluble. Examples of oil-soluble substances are:

- 4-aminobenzoic acid derivatives, preferably 2-ethylhexyl 4-(dimethylamino)benzoate, 2-octyl 4-(dimethylamino)benzoate and amyl 4-(dimethylamino)-benzoate;
- esters of salicylic acid, preferably 2-ethylhexyl salicylate, 4-isopropylbenzyl salicylate, homomenthyl salicylate;
- derivatives of benzophenone, preferably 2-hydroxy-4-methoxybenzophenone, 2-hydroxy-4-methoxy-4'-methyl-benzophenone, 2,2'-dihydroxy-4-methoxybenzophenone;
- esters of benzalmalonic acid, preferably di-2-ethylhexyl 4-methoxybenzmalonate;
- triazine derivatives, such as, for example, 2,4,6-trianilino (p-carbo-2'-ethyl-1'-hexyloxy)-1,3,5-triazine and octyl triazone, as described in EP 0818450 A1;
- propane-1,3-dione, such as, for example, 1-(4-tert-butylphenyl)-3-(4'-methoxyphenyl)propane-1,3-dione;
- ketotricyclo(5.2.1.0)decane derivatives, as described in EP 0694521 B1.

Suitable water-soluble substances are:
- 2-phenylbenzimidazole-5-sulfonic acid and the alkali metal, alkaline earth metal, ammonium, alkylammonium, alkanolammonium and glucammonium salts thereof;
- sulfonic acid derivatives of benzophenones, preferably 2-hydroxy-4-methoxybenzophenone-5-sulfonic acid and its salts;
- sulfonic acid derivatives of 3-benzylidenecamphor, such as, for example, 4-(2-oxo-3-bornylidene-methyl)benzenesulfonic acid and 2-methyl-5-(2-oxo-3-bornylidene) sulfonic acid and salts thereof.

In addition to the two abovementioned groups of primary light protection substances, it is also possible to use secondary light protection agents of the antioxidant type which interrupt the photochemical reaction chain which is triggered when UV radiation penetrates the skin. Typical examples thereof are amino acids (e.g. glycine, histidine, tyrosine, tryptophan) and derivatives thereof, imidazoles (e.g. urocanic acid) and derivatives thereof, peptides, such as D,L-carnosine, D-carnosine, L-carnosine and derivatives thereof (e.g. anserine), carotinoids, carotenes (e.g. α-carotene, β-carotene, lycopene) and derivatives thereof, chlorogenic acid and derivatives thereof, lipoic acid and derivatives thereof (e.g. dihydrolipoic acid), aurothioglucose, propylthiouracil and other thiols (e.g. thioredoxine, glutathione, cysteine, cystine, cystamine and the glycosyl, N-acetyl, methyl, ethyl, propyl, amyl, butyl and lauryl, palmitoyl, oleyl, γ-linoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts) and sulfoximine compounds (e.g. buthioninesulfoximines, homocystein-sulfoximines, buthioninesulfones, penta-, hexa-, hepta-thioninesulfoximine) in very low tolerated doses (e.g. pmol to µmol/kg), and also (metal) chelating agents (e.g. α-hydroxy fatty acids, palmitic acid, phytic acid, lactoferrin), α-hydroxy acids (e.g. citric acid, lactic acid, malic acid), humic acid, bile acid, bile extracts, bilirubin, biliverdin, EDTA, EGTA and derivatives thereof, unsaturated fatty acids and derivatives thereof (e.g. γ-linolenic acid, linoleic acid, oleic acid), folic acid and derivatives thereof, ubiquinone and ubiquinole and derivatives thereof, vitamin C and derivatives (e.g. ascorbyl palmitate, Mg ascorbyl phosphate, ascorbyl acetate), tocopherols and derivatives (e.g. vitamin E acetate), vitamin A and derivatives (vitamin A palmitate), and coniferyl benzoate of benzoin resin, rutinic acid and derivatives thereof, α-glycosylrutin, ferulic acid, furfurylidene-glucitol, carnosine, butylhydroxytoluene, butylhydroxy-anisole, nordihydroguaiacic acid, nordihydroguaiaretic acid, trihydroxybutyrophenone, uric acid and derivatives thereof, mannose and derivatives thereof, superoxide dismutase, zinc and derivatives thereof (e.g. ZnO, ZnSO$_4$), selenium and derivatives thereof (e.g. selenomethionine), stilbenes and derivatives thereof (e.g. stilbene oxide, trans-stilbene oxide) and derivatives (salts, esters, ethers, sugars, nucleotides, nucleosides, peptides and lipids) of said active ingredients which are suitable according to the invention.

To improve the flow behavior, it is also possible to use hydrotropic agents, such as, for example, ethanol, isopropyl alcohol or polyols. Polyols which are suitable here preferably have 2 to 15 carbon atoms and at least two hydroxyl groups. The polyols can also contain further functional groups, in particular amino groups, or be modified with nitrogen. Typical examples are:

glycerol;
alkylene glycols, such as, for example, ethylene glycol, diethylene glycol, propylene glycol, butylene glycol, hexylene glycol, and polyethylene glycols with an average molecular weight of from 100 to 1000 daltons;
technical-grade oligoglyceryl mixtures with an intrinsic degree of condensation of from 1.5 to 10, such as, for example, technical-grade diglyceryl mixtures with a diglyceryl content of from 40 to 50% by weight;
methylol compounds, such as, in particular, trimethylolethane, trimethylolpropane, trimethylolbutane, pentaerythritol and dipentaerythritol;
lower alkyl glucosides, in particular those having 1 to 8 carbon atoms in the alkyl radical, such as, for example, methyl and butyl glucoside;
sugar alcohols having 5 to 12 carbon atoms, such as, for example, sorbitol or mannitol,
sugars having 5 to 12 carbon atoms, such as, for example, glucose or sucrose;
amino sugars, such as, for example, glucamine;
dialcohol amines, such as diethanolamine or 2-amino-1,3-propanediol.

Suitable preservatives are, for example, phenoxyethanol, formaldehyde solution, parabens, petanediol or sorbic acid and the other classes of substance listed in Appendix 6, Part A and B of the Cosmetics Directive. Suitable insect repellents are N,N-diethyl-m-toluamide, 1,2-pentanediol or Insect Repellent 3535, and a suitable self-tanning agent is dihydroxyacetone.

Perfume oils which may be mentioned are mixtures of natural and synthetic fragrances. Natural fragrances are extracts from flowers (lily, lavender, rose, jasmine, neroli, ylang-ylang), stems and leaves (geranium, patchouli, petitgrain), fruits (aniseed, coriander, cumin, juniper), fruit peels (bergamot, lemon, orange), roots (mace, angelica, celery, cardamom, costus, iris, calmus), woods (pine wood, sandalwood, guaiac wood, cedarwood, rosewood), herbs and grasses (tarragon, lemon grass, sage, thyme), needles and branches (spruce, fir, pine, dwarf-pine), resins and balsams (galbanum, elemi, benzoin, myrrh, olibanum, opoponax). Also suitable are animal raw materials, such as, for example, civet and castoreum. Typical synthetic fragrance compounds are products of the ester, ether, aldehyde, ketone, alcohol and hydrocarbon type. Fragrance compounds of the ester type are, for example, benzyl acetate, phenoxyethyl iso-butyrate, p-tert-butylcyclohexyl acetate, linalyl acetate, dimethylbenzylcarbinyl acetate, phenylethyl acetate, linalyl benzoate, benzyl formate, ethylmethyl-phenyl glycinate, allyl cyclohexylpropionate, styrallyl propionate and benzyl salicylate. The ethers include, for example, benzyl ethyl ether, the aldehydes include, for example, the linear alkanals having 8 to 18 carbon atoms, citral, citronellal, citronellyloxyacetaldehyde, cyclamen aldehyde, hydroxycitronellal, lilial and bourgeonal, and the ketones include, for example, the ionones, α-isomethylionone and methyl cedryl ketone, the alcohols include anethole, citronellol, eugenol, isoeugenol, geraniol, linalool, phenylethyl alcohol and terpineol, and the hydrocarbons include predominantly the terpenes and balsams. Preference is, however, given to using mixtures of different fragrances which together produce a pleasing fragrance note. Essential oils of relatively low volatility, which are mostly used as aroma components, are also suitable as perfume oils, e.g. sage oil, camomile oil, oil of cloves, melissa oil, mint oil, cinnamon leaf oil, linden blossom oil, juniperberry oil, vetiver oil, olibanum oil, galbanum oil, labolanum oil and lavandin oil. Preference is given to using bergamot oil, dihydro-myrcenol, lilial, lyral, citronellol, phenylethyl alcohol, (x-hexylcinnamaldehyde, geraniol, benzyl-acetone, cyclamen aldehyde, linalool, boisambrene forte, ambroxan, indole, hedione, sandelice, lemon oil, mandarin oil, orange oil, allyl amyl glycolate, cyclovertal, lavandin oil, clary sage oil, β-damascone, geranium oil bourbon, cyclohexyl salicylate, Vertofix coeur, iso-E-Super, Fixolide NP, evernyl, iraldein gamma, phenylacetic acid, geranyl acetate, benzyl acetate, rose oxide, romilat, irotyl and floramat alone or in mixtures.

Dyes which can be used are the substances which are approved and suitable for cosmetic purposes, as are listed, for example, in the publication "Kosmetische Färbemittel" [Cosmetic Colorants] from the Farbstoff-konmmission der Deutschen Forschungsgemeinschaft [Dyes Commission of the German Research Council], Verlag Chemie, Weinheim, 1984, pp. 81-106. These dyes are normally used in concentrations of from 0.001 to 0.1% by weight, based on the total mixture.

Typical examples of antimicrobial agents are preservatives with specific action against Gram-positive bacteria, such as, for example, 2,4,4'-trichloro-2'-hydroxydiphenyl ether, chlorhexidine (1,6-di-(4-chlorophenylbiguanido) hexane) or TCC (3,4,4'-trichlorocarbanilide). Numerous fragrances and essential oils also have antimicrobial properties. Typical examples are the active ingredients eugenol, menthol and thymol in oil of cloves, mint oil and thyme oil. An interesting natural deodorant is the terpene alcohol farnesol (3,7,11-trimethyl-2,6,10-dodecatrien-1-ol), which is present in linden blossom oil and has a lily of the valley odor. Glycerol monolaurate has also proven useful as a bacteriostat. The proportion of additional antibacterial agents is usually about 0.1 to 2% by weight, based on the on the solids content of the preparations.

The total amount of additives may be 1 to 50% by weight, preferably 5 to 40% by weight, based on the agents. The agents can be prepared by customary cold or hot processes; preference is given to using the phase inversion temperature method.

EXAMPLES 601 g (2.9 mol) of partially hydrogenated coconut fatty acid, 303 g (2.08 mol), of adipic acid and 1.6 g of hypophosphorous acid were introduced into a tubular reactor and heated to 70° C. at a reduced pressure of 20 mbar. 618 g (4.15 mol) of triethanolamine were then added dropwise in portions and the temperature was increased at the same time to 120° C. When the addition was complete, the mixture was heated to 170° C., the pressure was reduced to 3 mbar and the mixture was stirred under these conditions for a period of 2.5 h until the acid number had dropped to a value below 5 mg of KOH/g. The mixture was then cooled to 60° C., the vacuum was interrupted by the introduction of nitrogen, and 0.6 g of hydrogen peroxide in the form of a 30% strength aqueous solution were added. For the quaternization, 500 g (1.46 mol) of the resulting ester were dissolved in 120 g of propylene glycol and admixed over a period of 1 h with 175 g (1.39 mol) of dimethyl sulfate at such a rate that the temperature does not exceed 60 to 70° C. When the addition is complete, the mixture is stirred for a further 2.5 h, the total nitrogen content being checked regularly by taking samples. The reaction was ended after a constant total nitrogen content is reached. A product with a solids content of 85% by weight was obtained.

Various preparations comprising esterquats, betaines, fatty acid amidoamines, nonionic surfactants and/or polyols were prepared. The results are summarized in Table 1. The viscosity was determined in accordance with Brookfield (mPas, 23° C., Spindel TF, 4 rpm). The appearance was observed after storage for 4 weeks at 23° C.

TABLE 1

Transparent softening agents - amounts in % by wt.

| Composition | 1 | 2 | 3 | 4 | 5 | 6 | 7 | 8 |
|---|---|---|---|---|---|---|---|---|
| Ester quat as in Example 1 | 52 | 39 | 59 | 40 | 19 | 14 | 5 | 90 |
| Dehyton ® PK Cocamido-propyl betaine A | 42 | 31 | — | — | — | — | — | — |
| Glucopon ® 215 CSUP Fatty alcohol C8-10 polyglycoside | — | — | — | — | 9 | 15 | — | — |
| Castor oil + 18 EO | — | — | — | 40 | — | — | — | — |
| Glycerol | — | — | 29 | — | 7 | 7 | 2 | — |
| Water | — | — | — | 10 | — | 4 | 2 | 5 |
| | | | | ad 100 | | | | |
| Appearance | clear | clear | clear | clear | clear | clear | clear | clear |

A) Condensation product of $C_{12/18}$-coconut fatty acid with dimethylaminopropylamine quaternized with dimethyl sulfate in 85% isopropanol

The invention claimed is:

1. A process for making a transparent softening agent comprising the steps of:
   (a) providing an esterquat made by:
      (i) reacting an alkanolamine and a mixture containing a fatty acid and a dicarboxylic acid, to form an ester;
      (ii) optionally, alkoxylating the ester to form an alkoxylated ester; and
      (iii) quaternizing the ester to form the esterquat;
   (b) providing a quaternized fatty acid amidoamine; and
   (c) mixing (a) and (b) together with water, whereby, a transparent softening agent is formed; and
   wherein the transparent softening agent is clear after storage for four weeks at 23° C.

2. The process of claim 1 wherein the fatty acid and dicarboxylic acid are employed in a molar ratio of from about 1:1 to 4:1.

3. The process of claim 1 wherein said alkanolamine and said mixture of fatty acid and dicarboxylic acid are employed in a molar ratio of from about 1:1.2 to 1:2.4.

4. The process of claim 1 wherein said alkanolamine comprises a trialkanolamine.

5. The process of claim 1 wherein the transparent softening agent contains from about 5 to 90% by weight of the esterquat.

6. The process of claim 5 wherein the transparent softening agent contains from about 30 to 40% by weight of the esterquat.

7. The process of claim 1 wherein the transparent softening agent contains from about 0.1 to 50% by weight of the quaternized fatty acid amidoamine.

8. The process of claim 7 wherein the transparent softening agent contains from about 2 to 10% by weight of the quaternized fatty acid amidoamine.

9. The product of the process of claim 1.

10. A softening agent comprising:
    (a) an esterquat containing residues of:
       (i) an alkanolamine;
       (ii) a mixture containing a fatty acid and a dicarboxylic acid;
       (iii) optionally, an alkylene oxide; and
       (iv) a quaternizing agent; and
    (b) a quaternized fatty acid amidoamine, and
    (c) water,
    wherein the softening agent is transparent and is clear after storage for four weeks at 23° C.

11. The agent of claim 10 wherein the fatty acid residues and dicarboxylic acid residues are present in a molar ratio of from about 1:1 to 4:1.

12. The agent of claim 10 wherein said alkanolamine and said mixture of fatty acid and dicarboxylic acid are present in a molar ratio of from about 1:1.2 to 1:2.4.

13. The agent of claim 10 wherein said alkanolamine comprises a trialkanolamine.

14. The agent of claim 10 wherein the transparent softening agent contains from about 5 to 90% by weight of the esterquat.

15. The agent of claim 14 wherein the transparent softening agent contains from about 30 to 40% by weight of the esterquat.

16. The agent of claim 10 wherein the transparent softening agent contains from about 0.1 to 50% by weight of the quaternized fatty acid amidoamine.

17. The agent of claim 16 wherein the transparent softening agent contains from about 2 to 10% by weight of the quaternized fatty acid amidoamine.

18. A cleaning composition containing the transparent softening agent of claim 10.

19. A softening agent consisting of:
    (a) an esterquat containing residues of:
       (i) an alkanolamine;
       (ii) a mixture containing a fatty acid and a dicarboxylic acid;

(iii) optionally, an alkylene oxide; and
(iv) a quaternizing agent; and
(b) a quaternized fatty acid amidoamine, and
(c) water,
wherein the softening agent is transparent and is clear after storage for four weeks at 23° C.

* * * * *